US007166456B2

(12) United States Patent
Lee et al.

(10) Patent No.: US 7,166,456 B2
(45) Date of Patent: Jan. 23, 2007

(54) MICROORGANISM FOR PRODUCING RIBOFLAVIN AND METHOD FOR PRODUCING RIBOFLAVIN USING THE SAME

(75) Inventors: Kwang Ho Lee, Yongin (KR); Young Hoon Park, Seongnam (KR); Jong Kwon Han, Yongin (KR); Jang Hee Park, Seoul (KR); Kyung Han Lee, Yongin (KR); Hyang Choi, Anyang (KR)

(73) Assignee: CJ Corp. (KR)

( * ) Notice: Subject to any disclaimer, the term of this patent is extended or adjusted under 35 U.S.C. 154(b) by 73 days.

(21) Appl. No.: 10/454,221

(22) Filed: Jun. 4, 2003

(65) Prior Publication Data

US 2004/0110249 A1    Jun. 10, 2004

(30) Foreign Application Priority Data

Dec. 5, 2002  (KR) ............... 10-2002-0076868

(51) Int. Cl.
*C12N 1/20* (2006.01)
*C12P 25/00* (2006.01)

(52) U.S. Cl. ..................... 435/252.5; 435/66
(58) Field of Classification Search ........... 435/252.5
See application file for complete search history.

(56) References Cited

U.S. PATENT DOCUMENTS

| 3,900,368 A | 8/1975 | Enei et al. ............... 195/96 |
| 5,231,007 A | 7/1993 | Heefner et al. ........... 435/66 |
| 5,837,528 A | 11/1998 | Perkins et al. ......... 435/252.31 |

FOREIGN PATENT DOCUMENTS

| EP | 0 405 370 A1 | 1/1991 |
| EP | 0 531 708 A2 | 3/1993 |
| EP | 0 531 708 A3 | 3/1993 |
| EP | 0 821 063 A2 | 1/1998 |
| EP | 1186664 * | 3/2002 |
| JP | 61-289893 | 12/1986 |
| JP | 62-11099 | 1/1987 |
| JP | 3-117489 | 5/1991 |
| JP | 5-64597 | 3/1993 |
| JP | 10-84978 | 4/1998 |
| KR | 344018 | 10/2001 |
| KR | 2001-0100222 | 11/2001 |
| KR | 330712 | 11/2001 |
| WO | WO 95/26406 | 10/1995 |

OTHER PUBLICATIONS

Gallori et al., Biochem. Biophys. Res. Commun., 85 (4), pp. 1518-1525, 1978.*
"Physiology and Metabolic Fluxes of Wild-Type and Riboflavin-Producing *Bacillus subtilis*"; Authors: Uwe Sauer, Vassily Hatzimanikatis, Hans-Peter Hohmann, Michael Manneberg, Adolphus P. G. M. Van Loon and James E. Bailey; XP-0022556992; American Society for Microbiology; Applied And Environmental Microbiology, vol. 62, No. 10; Oct. 1996; pp. 3687-3696.
Microbial Production of Riboflavin Using Riboflavin Overproducers, *Ashbya gossypii, Bacillus subtilis*, and *Candida famate*: An Overview; Authors: Seong Han Lim, Jong Soo Choi, and Enoch Y. Park ; XP008020356; Biotechnol. Bioprocess Eng., vol. 6, No. 2; 2001; pp. 75-88.
European Search Report; Application No. 03253625.2-2403-; Date of Completion: Oct. 17, 2003.
European Search Report; Application No. EP 90 11 1916; Date of Completion: Sep. 28, 1990.
"Genetic engineering of *Bacillus subtilis* for the commercial production of riboflavin"; Authors: J.B. Perkins, A. Sloma, T. Hernamm, K. Theriault, E. Zachgo, T. Erdenberger, N. Hannett, N.P. Chatterjee, V. Williams, II, G.A. Rufo, Jr., R. Hatch and J. Pero; Journal of Industrial Microbiology & Biotechnology, 22 ; Society for Industrial Microbiology; pp. 8-18; 1999.
The Merck Index, Merck & Co.; pp. 1183, 1184; 1983.
"Proline in the Osmoregulation of *Brevibacterium lactofermentum*"; Authors: Yoshio Kawahara, Tsuyoshi Ohsumi, Yasuhikp Yoshibara and Shigeho Ikeda; Agric. Biol. Chem., 53 (9); pp. 2475-2479; 1989.
"Osmotic Regulation of L-Proline Transport in *Salmonella typhimurium*"; Authors: Virginia Joan Dunlap and Laszio N. Csonka; Journal of Bacteriology; American Society for Microbiology; vol. 163, No. 1; pp. 296-304; Jul. 1985.

* cited by examiner

*Primary Examiner*—Nancy Vogel
(74) *Attorney, Agent, or Firm*—Cantor Colburn LLP

(57) ABSTRACT

Riboflavin-producing *Bacillus subtilis* which is resistant to proline analogue, and a method for producing riboflavin using the *Bacillus subtilis* are provided.

11 Claims, No Drawings

MICROORGANISM FOR PRODUCING RIBOFLAVIN AND METHOD FOR PRODUCING RIBOFLAVIN USING THE SAME

BACKGROUND OF THE INVENTION

This U.S. non-provisional application claims priority under 35 U.S.C. §119 to Korean Patent Application No. 2002-76868, filed on Dec. 5, 2002, in the Korean Intellectual Property Office, the contents of which are incorporated herein by reference in its entirety.

1. Field of the Invention

The present invention relates to a microorganism for producing riboflavin and a method for producing riboflavin using the same. More particularly, the present invention relates to a mutant of *Bacillus subtilis* with enhanced riboflavin productivity, when compared to the parent strain, and a method for producing riboflavin using the same.

2. Description of the Related Art

Riboflavin, also known as vitamin B2, is a water-soluble vitamin that is manufactured by biosynthesis of various microorganisms and plants. However, riboflavin cannot be biosynthesized in vertebrate including humans. Riboflavin is a precursor for flavin adenine dinucleotide (FAD) and flavin mononucleotide (FMN), coenzymes involved in the oxidation-reduction reactions of all cellular bodies, and thus is an essential nutrient for animals including humans. Deficiency of riboflavin may result in inflammation of the mouth and the mucous membrane of the pharynx, skin inflammation and other skin injuries, conjunctivitis, amblyopia, growth inhibition, and weight loss. Therefore, riboflavin is used as a vitamin product for prevention or treatment of diseases associated with the aforementioned vitamin deficiency or as a feed additive for raising livestock. In particular, concentrated riboflavin has been used as a feed by itself. The current worldwide production of riboflavin is 3,000 tones per year, of which 75% is used for feed additives and the remainder is used for food and pharmaceuticals.

Presently, riboflavin is produced by chemical synthesis or by fermenting microorganisms. In the chemical synthesis, highly pure riboflavin is produced by a multi-step process using a precursor such as D-ribose. However, due to a high cost of the starting material, the production cost is also high for chemical synthesis. Therefore, fermentation process of riboflavin by microorganisms was developed. Microorganisms for the fermentation process may be any riboflavin-producing microorganisms that exist in nature or riboflavin-overproducing microorganisms that are transformed by a genetic engineering, chemical, or physical process. These microorganisms are cultured under an appropriate condition to produce riboflavin. The produced riboflavin is recovered from the culture.

Microorganisms widely known for riboflavin production are *Saccharomyces* sp. and *Candida* sp. belonging in the yeast group, *Clostridium* sp., *Bacillus* sp., and *Corynebacterium* sp. belonging in the bacteria group, and *Eremothecium* sp. and *Ashbya* sp. belonging in the fungi group.

U.S. Pat. No. 5,231,007 discloses a method for producing riboflavin using *Candida famata* yeast. It was reported that genetically engineered *Bacillus subtilis* and *Corynebacterium ammoniagenes* which overexpress the genes of the enzymes involved in riboflavin biosynthesis produced riboflavin of 4.5 g/l and 17.4 g/l, respectively [Perkins et al., *J. Ind. Microbiol. Biotechnol.*, 22:8–18, 1999]. European Patent No. EP 0 821 063 discloses a method for producing riboflavin using a recombinant *Bacillus subtilis*. U.S. Pat. No. 5,837,528 discloses a recombinant strain of *Bacillus subtilis* for overproducing riboflavin obtained by introducing the rib operon into the parent strain using a recombinant technology. In addition, there are *Eremothecium ashbyii* and *Ashbya gossypii* ascomycete fungi which were reported by Windholz et al. [The Merck Index, Merck & Co., p. 1183, 1983] as microorganisms for riboflavin production. In particular, it was reported that culture of mutants of these ascomycete fungi in nutrient media containing molasses or vegetable oil as a main carbon source resulted in 15 g of riboflavin per 1 liter of a fermentation solution [Bigelis, *Biotechnology*, vol. 7b, p. 243, 1989]. Production of riboflavin using *Ashbya gossypii* is also disclosed in WO95/26406.

However, development of microorganisms with enhanced riboflavin productivity for mass-production of riboflavin is still in need.

Meanwhile, in the fermentation method using microorganism, a strain of microorganism with osmopressure resistance is being developed to obtain culture products in high concentration and and high yield. The strain of microorganism with osmopressure resistance is capable of producing culture products in high yield because its growth and metabolism are not inhibited by increase in the external osmopressure caused by excess carbon sources and accumulation of culture products. On the basis of the foregoing, the present inventors developed a strain of microorganism that produce 5'-inosinic acid in high concentration and in high yield by developing a strain of microorganism resistant to proline analogue to enhance its ability of proline biosynthesis and thereby reinforced its osmopressure resistance characteristic of the microorganism, which is disclosed in KR Patnet No. 330712.

SUMMARY OF THE INVENTION

The present invention provides riboflavin-producing *Bacillus subtilis* which is resistant to proline analogue.

The present invention also provides a method for producing riboflavin using the *Bacillus subtilis*.

According to an aspect of the present invention, there is provided riboflavin-producing *Bacillus subtilis* which is resistant to proline analogue. Preferably, *Bacillus subtilis* CJKB0001 is used (accession number: KCCM-10445).

While searching for microorganisms with enhanced riboflavin productivity, the present inventors found that inducing mutation on *Bacillus subtilis* and introducing proline analogue resistance to it result in osmopressur resistance and the enhancement of productivity of riboflavin. Among these strains, the present inventors selected riboflavin-overproducing and high yielding strains and produced riboflavin in large scale using the selected strains.

According to another aspect of the present invention, there is provided a method for producing riboflavin comprising culturing the *Bacillus subtilis* and recovering riboflavin from the culture.

The subject *Bacillus subtilis* referred to as *Bacillus subtilis* CJKB0001 has the accession number KCCM-10445, having been deposited in Korean Culture Center of Microorganisms (KCCM), 361-221, Yurim B/D, Hongje-1-dong, Seodaemun-gu, Seoul 120-091, Republic of Korea, on Nov. 18, 2002.

DETAILED DESCRIPTION OF THE INVENTION

Hereinafter, the present invention will be described in detail.

The *Bacillus subtilis* of the present invention is a mutant of *Bacillus subtilis* AS5. Because it is resistant to proline analogue, and it produces increased proline biosynthesis, leading to enhanced osmopressure resitsance. Therefore, it produces high concentration of riboflavin in high yield.

Most microorganisms increase the osomopressure in the internal bacteria body by accumulating potassium ions and organic solutes called osmolytes, so as to prevent osmotic dehydration, when the osmopressure in the external bacteria body is increased. The osmolytes include, but are not limited to L-proline, glutamic acid, sugar, and N-methylated amino acid derivatives. Among them, L-proline is known to be a critical factor of osmopressure regulation. It is reported that as the osmopressure in the external *Brevibacterium lactofermentum* increases, the activity of pyrroline-5-carboxylate reductase which is a critical enzyme of L-proline biosynthesis, increase, thereby resulting in the accumulation of L-proline in the internal bacteria body [Agr, Bio, chem., 53(9):2475–2479, 1989]. Additionally, there have been a report on the accumulation of L-proline in the internal bacteria body of *Escherichia coli, Salmonella typhimurium, Serratia marcescens*, etc. caused by the osmopressure on the external bacteria body [J. Bacteriol., 163:296,1985].

Therefore, the present inventors induced mutation on *Bacillus subtillus* AS5 to give osmopressure resistance, and then selected the mutants with proline analogue resistance which can grow in the culture media containg high concentration of proline analogue. Among them, one mutant with the highest riboflavin productivity was selected.

The proline analogue includes, but are not limited to 3,4-dehydroproline, L-azetidine-2-carboxylic acid, thiaproline, L-thiazolidine-4-carboxylic acid, (S)-2,2-dimethyl-4-oxazolidecarboxylic acid, (S)-5,5-dimethyl-4-thiazolidecarboxylic acid, (4S, 2RS)-2-ethyl-thiazolidine-4-carboxylic acid, (2S, 4S)-4-hydroxy-2-pyrroline-carboxylic acid, 2-piperidinecarboxylic acid, and 2,5-pyrrolidinedione.

The parent strain as used herein is *Bacillus subtilis* AS5 (BIONOM-S, Moscow, Russia).

Conventional physical or chemical processes can induce mutation on the parent strain. For example, the parent strain may be exposed to X-rays or UV light, or a chemical agent such as N-methyl-N'-nitro-N-nitrosoguanidine (NTG), diethylsulfate, and ethylamine.

The present inventors cultured mutation-induced strains in media containing various concentrations of thiaproline as proline analogue. Mutants capable of growing in the presence of a high concentration of thiaproline were selected. Among them, one mutant with the highest riboflavin productivity was selected. The selected mutant was designated as *Bacillus subtilis* CJKB0001 and deposited in the Korean Culture Center of Microorganisms on Nov. 18, 2002 (accession number: KCCM-10445).

The *Bacillus subtilis* CJKB0001 (KCCM-10445) of the present invention can grow in even up to 70 mg/l of thiaproline-containing medium. On the other hand, the *Bacillus subtilis* AS5 as the parent strain cannot grow in the presence of more than 40 mg/l of thiaproline.

Therefore, the *Bacillus subtilis* CJKB0001 (KCCM-10445) of the present invention has proline analogue resistance and, even when a high concentration of solutes accumulate in the external bacteria body, the *Bacillus subtilis* CJKB0001 can accumulate a high concentration of riboflavin in a culture medium by acccumulating a high concentration of proline in the internal bacteria body and thereby effectively preventing the inhibition of its growth and metabolism caused by osmopressure, in comparison with the parent strain.

In addition, the present inventors noticed that the *Bacillus subtilis* CJKB0001 (KCCM-10445) of the present invention accumulated 8.0 g/l of riboflavin which is 11% higher than that of the *Bacillus subtilis* AS5 in a flask culture and they also accumulated 26.8 g/l of riboflavin which is 19.6% higher than that of the parent strain in a 5-liter fermenter culture.

Therefore, the *Bacillus subtilis* CJKB0001 (KCCM-10445) of the present invention has enhanced resistance to proline analogue and has substantially enhanced riboflavin productivity by having osmopressure resistance, when compared to the *Bacillus subtilis* AS5.

In order to produce riboflavin, the *Bacillus subtilis* CJKB0001 (KCCM-10445) of the present invention is cultured under a suitable condition.

In detail, the *Bacillus subtilis* CJKB0001 (KCCM-10445) is inoculated onto a conventional medium containing a suitable carbon source, nitrogen source, and inorganic compounds and cultured at a predetermined temperature and pH under an aerobic condition. Examples of the carbon source include glucose, molasses, lactose, sucrose, maltose, dextrin, starch, mannitol, sorbitol, and glycerol. Preferably, glucose and molasses are used. Examples of the nitrogen source include an inorganic source such as ammonia, ammonium chloride, and ammonium sulfate and an organic source such as peptone, NZ-amine, beef extract, yeast extract, corn steep liquor, casein hydrolysate, fish or fish meal, and defatted soybean cake or meal. Preferably, yeast extract and corn steep liquor are chosen. Examples of the inorganic compounds include potassium monohydrogen phosphate, potassium dihydrogen phosphate, magnesium sulfate, ferrous sulfate, manganese sulfate, and calcium carbonate. When needed, vitamins and auxotrophic bases may be used. For the culture, shaking culture or stirring culture by aeration may be used. The culture temperature ranges from 30 to 45° C., and preferably 37 to 40° C. During the culture, preferably, the pH is adjusted to a fairly neutral level. The culture period is 5 to 6 days.

According to one embodiment of the present invention, the *Bacillus subtilis* CJKB0001 (KCCM-10445) was inoculated onto a seed medium and cultured at an aeration flow rate of 1 vvm, 37° C., and 800 rpm for 20 hours. The seed culture was inoculated onto a fermentation medium and was subjected to shaking culture at an aeration flow rate of 1 vvm, 40° C., 800 rpm, and pH 7.0 for 60 to 70 hours. During the shaking culture, the fermentation culture was supplied with a glucose supplement medium to maintain the residual glucose in the culture to a level of 0.5 to 1% until the total content of glucose in the fermentation culture reached 20%. Riboflavin was yielded at an increased level of about 19.6%, when compared to the parent strain.

Hereinafter, the present invention will be described more specifically by examples. However, the following examples are provided only for illustrations and thus the present invention is not limited to or by them.

EXAMPLE 1

Selection of *Bacillus subtilis* CJKB0001 of the Present Invention

In order to obtain the *Bacillus subtilis* CJKB0001 of the present invention, the *Bacillus subtilis* AS5 as the parent strain was subjected to mutation. Then, the mutants of the *Bacillus subtilis* AS5 were cultured in thiaproline-containing media to obtain colonies. Among these colonies, a mutant strain with the highest riboflavin productivity was selected as the *Bacillus subtilis* CJKB0001.

The *Bacillus subtilis* AS5 as the parent strain was obtained from BIONOM-S, Ltd. (Obolensk, Moscow, Russia). The *Bacillus subtilis* AS5 was suspended in phosphate buffer at pH 7.0 or citrate buffer at pH 5.5 to have a cell density of $10^7$ to $10^8$ cells/ml. A mutation-inducing agent, N-methyl-N'-nitro-N-nitrosoguanidine was added to the suspension until its concentration was 10 to 50 µg/ml. The resultant mixture was incubated at room temperature or 30° C. for 30 to 60 minutes to induce mutation. Then, the mixture was washed three times with 0.85% of saline solution and diluted in an appropriate manner. The diluted solution was plated onto 1.8% agar-containing minimal media with various concentrations of thiaproline and cultured at 37° C. for 5 days to obtain colonies. In this case, the concentration of thiaproline ranged from 0 mg/l to 100 mg/l. The formed colonies were inoculated onto nutrient agar media and cultured at 37° C. for 24 hours. Then, the resultant nutrient cultures were inoculated onto fermentation media and cultured at 37° C. for 4 to 5 days. The highest riboflavin-producing strain was selected. Each medium composition is presented in Table 1.

TABLE 1

Compositions of media for selection of *Bacillus subtilis* CJKB0001 of the present invention

| Medium | Composition |
|---|---|
| Nutrient agar medium | 10 g/l of tryptose, 3 g/l of beef extract, 5 g/l of sodium chloride, 15 g/l of agar, pH 7.2 |
| Minimal medium | 2.5 g/l of glucose, 7 g/l of monopotassium phosphate, 3 g/l of dipotassium phosphate, 0.5 g/l of sodium citrate, 0.75 g/l of magnesium sulfate 7-hydrate, 0.5 g/l of yeast extract, 0.15 g/l of casamino acid, 20 mg/l of tryptophan, pH 7.2 |
| thiaproline-containing medium | 20 to 100 mg/l of thiaproline + minimal medium |
| Fermentation medium | 100 g/l of glucose, 20 g/l of dry yeast, 5 g/l of corn steep liquor, 0.5 g/l of magnesium sulfate 7-hydrate, 1.5 g/l of monopotassium phosphate, 3.5 g/l of dipotassium phosphate, 6 g/l of urea, 10 mg/l of erythromycin, 10 mg/l of chloramphenicol, pH 7.2 to 7.4 |

The productivity of riboflavin was measured by HPLC. HPLC was performed using waters 510 coupled with kromasil C18 (5 µm) column (inner diameter: 4.6 mm, length: 250 mm). A mixed solvent of 5 mM of sodium hexanesulfonate and 20 mM of $H_3PO_4$, and acetonitrile (89:11, v/v) was used as a mobile phase. The flow rate of the mobile phase was 1 ml/min. The injection amount of samples was 15 µl, and distilled water for sample dilution were used. In addition, UV detector (TSP UV2000, UV 260 nm) was used as a detector.

According to the test results, mutants which grew on 70 mg/l of thiaproline-containing media exhibited excellent riboflavin productivity. Among them, one mutant with the highest riboflavin productivity was selected and designated as *Bacillus subtilis* CJKB0001. The *Bacillus subtilis* CJKB0001 was deposited in the Korean Culture Center of Microorganisms on Nov. 18, 2002 under accession number: KCCM-10445.

EXAMPLE 2

Evaluation of Resistance of *Bacillus subtilis* CJKB0001 and *Bacillus subtilis* AS5 Against Thiaproline In this example, in order to evaluate resistance to thiaproline, the *Bacillus subtilis* CJKB0001 (KCCM-10445) of Example 1 and the *Bacillus subtilis* AS5 as the parent strain were cultured in various concentrations of thiaproline-containing media. In detail, respective strains were inoculated onto thiaproline-containing media as shown in Table 1 and cultured at 37° C. for 5 days. In this case, the concentration of thiaproline ranged from 0 to 100 mg/l.

According to the test results as shown in Table 2, the *Bacillus subtilis* AS5 could not grow in more than 40 mg/l of thiaproline-containing media. On the other hand, the *Bacillus subtilis* CJKB0001 (KCCM-10445) of the present invention could grow even in a 70 mg/l of thiaproline-containing medium.

TABLE 2

Evaluation of resistance of *Bacillus subtilis* CJKB0001 and *Bacillus subtilis* AS5 against thiaproline

| Strain | Concentration of thiaproline (mg/l) | | | | | |
|---|---|---|---|---|---|---|
| | 0 | 20 | 40 | 50 | 70 | 100 |
| *Bacillus subtilis* AS5 | +++ | ++ | + | − | − | − |
| *Bacillus subtilis* CJKB0001 (KCCM-10445) | +++ | +++ | +++ | ++ | + | − |

+: growth,
−: not growth

EXAMPLE 3

Potency of Fermentation of *Bacillus subtilis* CJKB0001 of the Present Invention in Flask The potencies of fermentation of the *Bacillus subtilis* CJKB0001(KCCM-10445) and the *Bacillus subtilis* AS5 in flasks were evaluated. Each strain was inoculated onto a seed medium and cultured. Then, each seed culture was transferred to a fermentation medium in a flask. The seed medium was prepared by distributing 5 ml of a seed medium in a test tube with a diameter of 18 mm and sterilizing the test tube under pressure at 121° C. for 15 minutes. Each of the *Bacillus subtilis* CJKB0002 and the *Bacillus subtilis* AS5 was inoculated onto the seed medium and shaking culture was performed at 200 rpm and 37° C. for 20 hours. When the seed culture was completed, 1 ml of each seed culture was inoculated onto a fermentation medium in a flask and shaking culture was performed at 200 rpm and 37° C. for 90 hours. The fermentation medium was prepared by sterilizing a medium FA and a medium FS under pressure in the same manner as in the preparation of the seed medium and distributing 15 ml of the medium FA and 5 ml of the medium FS into a 250 ml shaking culture flask that was pre-sterilized under pressure. When the fermentation was completed, the concentration of riboflavin accumulated in the fermentation culture was measured in the same manner as in Example 1. Each composition of the seed medium and fermentation medium as used in this example are presented in Table 3.

TABLE 3

Compositions of media for fermentation in flask

| Medium | Composition |
|---|---|
| Seed medium | 5 g/l of yeast extract, 10 g/l of tryptone, 10 g/l of sodium chloride, No adjustment to pH |
| Fermentation medium | Medium FA: 100 g/l of glucose, 20 g/l of dry yeast, 0.5 g/l of magnesium sulfate 7-hydrate<br>medium FS: 1.5 g/l of monopotassium phosphate, 3.5 g/l of dipotassium phosphate, 6 g/l of urea, 10 mg/l of erythromycin, 10 mg/l of chloramphenicol pH: 7.2 to 7.4 |

According to the test results, the *Bacillus subtilis* AS5 as the parent strain produced 7.2 g/l of riboflavin. On the other hand, the *Bacillus subtilis* CJKB0001 (KCCM-10445) of the present invention produced 8.0 g/l of riboflavin, which was 11% higher than in the *Bacillus subtilis* AS5.

EXAMPLE 4

Potency of Fermentation of *Bacillus subtilis* CJKB0001 of the Present Invention in 5-Liter Fermenter The potencies of fermentation of the *Bacillus subtilis* CJKB0001 (KCCM-10445) and the *Bacillus subtilis* AS5 in 5-liter fermenters were evaluated in a comparative manner. Each strain was inoculated onto a seed medium and cultured. Then, each seed culture was inoculated onto a fermentation medium and fed-batch cultured. For this, first, 1 liter of each seed medium was distributed in a laboratory fermenter with capacity of 2.5 liter and sterilized under pressure at 121° C. for 10 minutes to prepare a seed medium. After the seed medium was cooled, 10 ml of each suspension of the *Bacillus subtilis* CJKB0001 and the *Bacillus subtilis* AS5 in saline solution was inoculated onto the seed culture. Then, each strain-containing seed culture was incubated under sterile aeration at a rate of 1 vvm at 37° C. and 800 rpm for 20 hours. During the seed culture, pH was not adjusted. After the seed culture was completed, each seed culture was inoculated onto a fermentation medium and fed-batch cultured. The fermentation medium was prepared by distributing 1.4 liter of a fermentation medium in a laboratory fermenter with capacity of 5 liter, followed by pressure sterilization at 121° C. for 20 minutes. After the fermentation medium was cooled, 200 ml of each seed culture was inoculated onto the fermentation medium and cultured under aeration at a rate of 1 vvm at 800 rpm and 40° C. During the fermentation, each fermentation culture was supplied with a glucose supplement medium to maintain the residual glucose in the culture to a level of 0.5 to 1% until the total content of glucose in the fermentation culture reached 20%. During the fermentation, pH was maintained to 7.0 using aqueous ammonia. The fermentation period was 60 to 70 hours. When the fermentation was completed, the concentration of riboflavin accumulated in the fermentation culture was measured in the same manner as in Example 1. Each composition of the seed medium and fermentation medium as used in this example are presented in Table 4.

TABLE 4

Compositions of media for culture in 5-liter fermenter

| Medium | Composition |
|---|---|
| Seed medium | 30 g/l of molasses (50%, based on glucose), 15 g/l of corn steep liquor, 0.5 g/l of magnesium sulfate 7-hydrate, 5 g/l of ammonium sulfate, 1.5 g/l of monopotassium phosphate, 3.5 g/l of dipotassium phosphate, 10 mg/l of erythromycin, 10 mg/l of chloramphenicol, pH 7.4 |
| Fermentation medium | Medium FA: 20 g/l of dry yeast, 5 g/l of corn steep liquor, 2 g/l of ammonium sulfate, 0.5 g/l of magnesium sulfate 7-hydrate, 17.5 g/l of monopotassium phosphate, 7.5 g/l of dipotassium phosphate, 5 mg/l of erythromycin, 10 mg/l of chloramphenicol, pH 7.2–7.4<br>Supplement medium: 620 g/l of glucose, 26.7 g/l of dry yeast, 26.7 g/l of corn steep liquor |

According to the test results, the *Bacillus subtilis* AS5 as the parent strain produced 22.4 g/l of riboflavin. On the other hand, the *Bacillus subtilis* CJKB0001 (KCCM-10445) of the present invention produced 26.8 g/l of riboflavin, which was about 19.6% higher than in the *Bacillus subtilis* AS5.

As apparent from the above description, the *Bacillus subtilis* of the present invention has high resistance to proline analogue and has increased synthesis of proline in the inside of the bacteria body to get enhanced osmotic pressure, resulting in producing a high concentration of riboflavin in high yield. Therefore, a large amount of riboflavin can be yielded.

What is claimed is:

1. A method for producing riboflavin comprising:
   culturing a *Bacillus subtilis* strain which is resistant to proline analogue and;
   recovering riboflavin from the culture.

2. The method of claim 1, wherein the *Bacillus subtilis* strain includes is *Bacillus subtilis* CJKB0001 (KCCM-10445) strain.

3. A riboflavin producing *Bacillus subtilis* CJKB0001 (KCCM-10445) strain.

4. A method of producing a *Bacillus subtilis* strain with enhanced riboflavin producing ability, comprising:
   inducing a mutation in a parent *Bacillus subtilis* strain; and
   selecting a *Bacillus subtilis* mutant strain with enhanced proline analogue resistance compared to the parent *Bacillus subtilis* strain,
   wherein the *Bacillus subtilis* mutant strain is a *Bacillus subtilis* strain with enhanced riboflavin producing ability compared to the parent *Bacillus subtilis* strain.

5. The method of claim 4, wherein inducing a mutation in a parent *Bacillus subtilis* strain comprises inducing the mutation in the parent *Bacillus subtilis* strain by a physical process or a chemical process.

6. The method of claim 5, wherein the physical process includes exposing the parent *Bacillus subtilis* strain to X-ray or UV light.

7. The method of claim 5, wherein the chemical process includes applying a chemical agent to the parent *Bacillus subtilis* strain.

8. The method of claim 7, wherein the chemical agent includes N-methyl-N'-nitro-N-nitrosoguanidine, diethylsulfate, or ethylamine.

9. The method of claim 4, wherein an amount of the riboflavin produced in the *Bacillus subtilis* mutant strain is at least 11% higher than an amount of the riboflavin produced in the parent *Bacillus subtilis* strain.

10. The method of claim of claim 4, wherein the *Bacillus subtilis* mutant strain includes is *Bacillus subtilis* CJKB0001 (KCCM-10445) strain.

11. A method for producing riboflavin comprising:

culturing *Bacillus subtilis* CJKB0001 (KCCM-10445); and recovering riboflavin from the culture.

* * * * *